United States Patent [19]

Sitek et al.

[11] Patent Number: 4,522,788
[45] Date of Patent: Jun. 11, 1985

[54] PROXIMATE ANALYZER

[75] Inventors: George J. Sitek; Sherman L. Walker, both of Stevensville, Mich.

[73] Assignee: Leco Corporation, St. Joseph, Mich.

[21] Appl. No.: 355,221

[22] Filed: Mar. 5, 1982

[51] Int. Cl.³ ............................................. G01N 31/12
[52] U.S. Cl. ..................................... 422/78; 422/104; 177/50; 177/55
[58] Field of Search .......................... 422/64, 78, 104; 436/157, 160; 177/50, 54, 55

[56] References Cited

U.S. PATENT DOCUMENTS

| 4,009,605 | 3/1977 | Kober | 436/157 |
| 4,248,315 | 2/1981 | Falinower | 422/64 |
| 4,303,615 | 12/1981 | Jarmell et al. | 422/78 |

FOREIGN PATENT DOCUMENTS 653513  5/1951  United Kingdom .
702578  1/1954  United Kingdom .

OTHER PUBLICATIONS

CEM Corp., Moisture/Solids Analyzer AVC-80, 1981.
ASTM Standards D 3172-73, D 3173-73, D 3174-73, D 3175-77, 1979.
Fisher Scientific Co., Sulfur Analyzer Model 475, 4/81.

Primary Examiner—Hiram H. Bernstein
Attorney, Agent, or Firm—Price, Heneveld, Huizenga & Cooper

[57] ABSTRACT

The specification discloses a proximate analyzer for the analysis of fossil fuels such as coal and coke. The analyzer includes a temperature-controllable and atmosphere-controllable furnace chamber, a balance having a weigh platform positioned within the furnace chamber, and a platter positioned within the chamber and adapted to support a plurality of sample-containing crucibles. The furnace further includes means for continuously depositing the crucibles in a predetermined sequence on the weigh platform and means for monitoring the weights of the crucibles to determine when analysis is complete and for calculating the proximate analysis results based on weight loss. A method of proximate analysis using the proximate analyzer is also disclosed.

8 Claims, 9 Drawing Figures 4,522,788

PROXIMATE ANALYZER

BACKGROUND OF THE INVENTION

The present invention relates to proximate analyzers, and more particularly analyzers which heat the sample during analysis.

The proximate analysis of a material to determine the content of at least some of its constituent components provides important information regarding the material. This is particularly true with coal and coke, which are composed primarily of the four components moisture, volatiles, fixed carbon, and ash. Coal and coke proximate analysis results are useful in predicting energy content, potential pollution problems, and the ash which will remain after burning.

The ASTM standards for determining the moisture, volatiles, fixed carbon, and ash content of coal and coke are relatively complex. Each of the moisture, volatiles, and ash content determinations are made by first weighing a sample to be analyzed, second subjecting the sample to elevated temperatures in a controlled atmosphere for a standard period of time, and third weighing the sample to determine sample weight loss. Well-known mathematical formulas are then utilized to calculate the moisture, volatiles, fixed carbon, and ash content of the material. The samples must be repeatedly handled and weighed during testing. The handling is time consuming and can be dangerous because of the high temperatures involved. Further, because the sample must be left in the furnace for a fixed period of time, the tests are relatively time-consuming with no provision made for rapidly analyzing a sample analyzable in less then the standard time periods.

Although analyzers have been developed for facilitating the proximate analysis of coal and coke, these analyzers are not without their drawbacks. One such analyzer includes a furnace and a balance having a weigh platform positioned in the furnace. Consequently, a sample, or sample-containing crucible, may be placed on the balance to provide a constant readout of sample weight during the heating period. However, only one sample may be analyzed during each analyzer cycle. Another device includes a rack containing a plurality of samples, or sample-containing crucibles, and a furnace in which the rack is positioned. Although this analyzer is capable of heating a plurality of samples simultaneously, the individual samples must be handled and weighed outside of the furnace both before and after heating.

SUMMARY OF THE INVENTION

The aforementioned problems are solved by the present invention. Essentially, a proximate analyzer is provided including a furnace chamber, an electronic balance having a weigh platform within the furnace chamber, a sample rack within the furnace chamber adapted to support a plurality of sample-containing crucibles, and means for continuously and individually depositing the crucibles in a predetermined sequence on the weigh platform. Additionally, a circuit means is operatively coupled to the balance for receiving weight interpretation signals therefrom for monitoring the individual weights of the crucibles to determine the weight loss of the samples during heating and to calculate proximate analysis results.

Consequently, the analyzer is capable of analyzing a plurality of samples during one analyzer cycle. The samples are not handled after being loaded into the furnace because all weighing is conducted automatically within the furnace chamber. This improves accuracy of measurement and eliminates the danger of handling the heated crucibles. Third, because the weights of the samples are continually monitored, the circuit means can analyze the weighings to determine when analysis is complete, for example when the weights of the samples attain a relatively constant value or constant rate of change indicating that the constituent component driven from the samples during the particular temperature and environmental conditions has been eliminated from the sample. Such monitoring reduces analysis time since the samples need not be left in the furnace any longer than necessary to conduct the analysis.

These and other objects, advantages, and features of the invention will be more fully understood and appreciated by reference to the written specification and appended drawings.

DESCRIPTION OF THE PREFERRED EMBODIMENT

Figure 1:
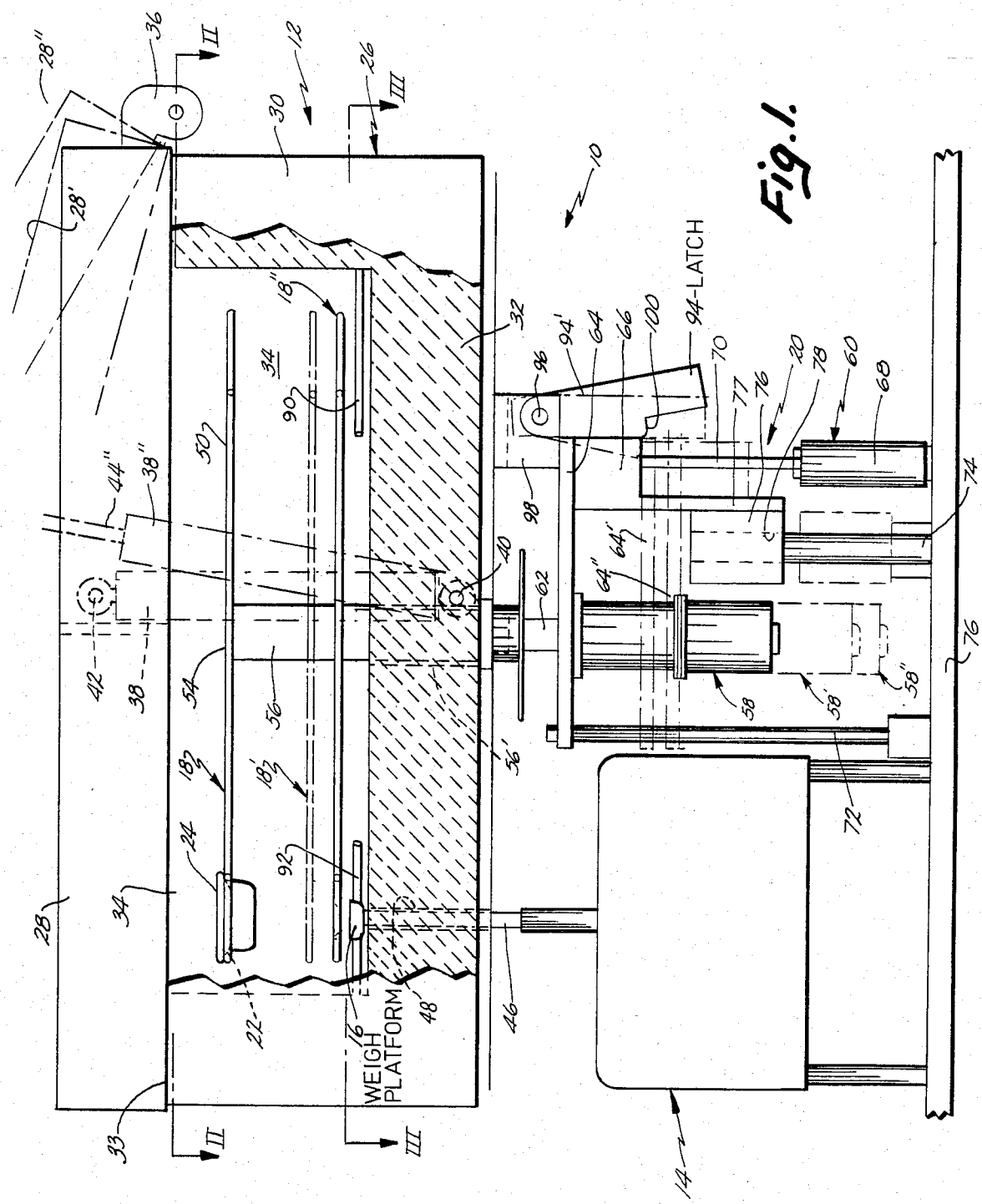
FIG. 1 is a side elevational view, partially broken away, of the proximate analyzer of the present invention.
Figure 2:
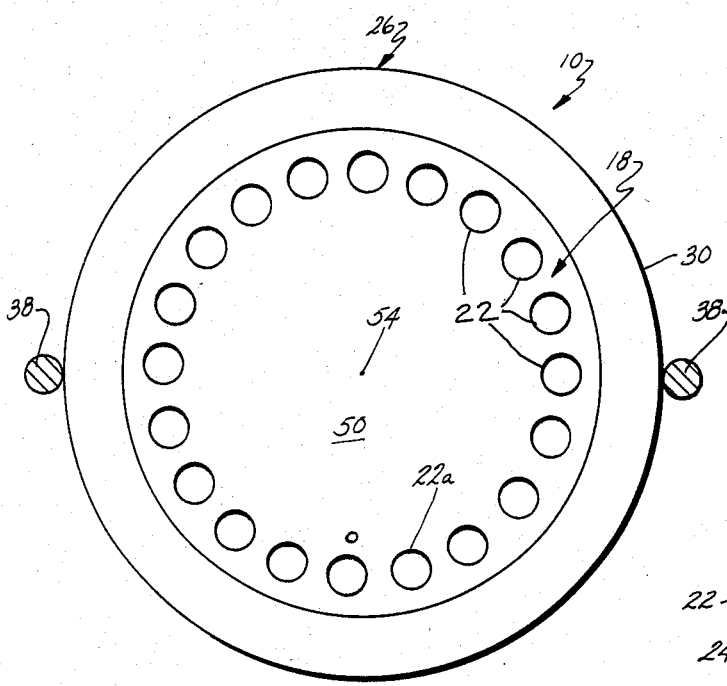
FIG. 2 is a view taken along plane II—II in FIG. 1.

A fossil fuel proximate analyzer in accordance with a preferred embodiment of the invention is illustrated in the drawings and generally designated 10. As seen in FIG. 1, analyzer 10 includes a furnace 12, an electronic balance 14 having weigh platform 16 positioned within the furnace, a sample platter 18 positioned within the furnace, and a platter operation mechanism 20 supporting platter 18 within the furnace. Sample rack 18 is a disc having a plurality of apertures 22 positioned evenly about the periphery of the platter (see also FIG. 2). A plurality of sample-containing crucibles 24 may be positioned on platter 18 with one of the crucibles generally aligned with each one of apertures 22 and supported by the peripheral edge of the aperture. Mechanism 20 is then actuated to continuously and individually deposit crucibles 24 on weigh platform 16 by rotating platter 18 so that one of apertures 22 is aligned with weigh platform 16 and then lowering platter 18 to deposit the associated crucible on the weigh platform. After weighing is complete, platter 18 is shifted upwardly to lift the weighed crucible off of weigh platform 16, and the next adjacent crucible is weighed in a similar manner. Consequently, crucibles 24 may be weighed within furnace 12 without opening the furnace.

Referring more specifically to the construction of furnace 12 (FIG. 1), it is seen that the furnace includes lower containing member 26 and a cover 28, which together define a chamber 34 having a volume of approximately three liters. Lower member 26 includes a generally cylindrical side wall 30 integrally joined to generally horizontal, planar furnace floor 32 (see also FIG. 3). The upper end of member 26 is open with wall 30 terminating with an annular top surface 33. Cover 28 is a generally planar member having a circular shape and, when closed, rests on the upper surface 33 of wall 30. Conventional heating elements (not shown) are positioned within furnace 12 and are controlled with a suitable temperature controller capable of regulating the temperature therein at desired temperatures between 50° C. and 1,000° C. Both lower member 26 and cover 28 are fabricated from well-known refractory ceramic materials such as alumina. Cover 28 is hingedly secured to member 26 by a hinge 36 for movement between a closed position resting on surface 33 of lower member 26 as indicated in FIG. 1, a load position indicated in phantom at 28′, and an open position indicated in phantom as 28″. A pair of conventional pneumatic cylinders 38 are mounted on opposite sides of furnace 12 (see also FIG. 2) and are pivotally mounted to and between member 26 and cover 28 at pivot points 40 and 42, respectively. Each cylinder 38 includes a rod 44 which is telescopically received within the cylinder body and telescopes outwardly therefrom when pneumatic pressure is applied to the cylinder to move cover 28 between the closed, load 28′, and open 28″ positions. When cover 28 is in its fully open position 28″, cylinders 38 are positioned as indicated in FIG. 1 at 38″.

The electronic balance 14 includes a weigh platform 16 supported on shaft 46. Shaft 46 extends vertically and is located within a generally cylindrical bore 48 formed in furnace floor 32. The inside diameter of bore 48 is somewhat larger than the outer diameter of shaft 46 so that the shaft is freely movable within the bore.

Sample platter 18 (FIGS. 1 and 2) comprises a generally planar, circult disc-shaped plate 50 capable of withstanding temperatures of 1000° C. Plate 50 includes twenty evenly spaced circular apertures 22 extending therethrough near the outer periphery of the platter. One aperture 22a is designated the zero-position aperture, and each of apertures 22 has generally the same diameter. The circular configuration of apertures 22 and plates 50 has a common axis 54 about which sample platter 18 rotates. Since the center of each aperture is the same distance from axis 54, by rotating platter 18, any one of apertures 22 may be vertically aligned with weigh platform 16.

Elevation and rotation means 20 are provided to selectively raise platter 18, rotate the platter, and subsequently lower the platter to sequentially place a sample-holding crucible 24 on weigh platform 16. Means 20 (FIG. 1) includes a shaft 56 supporting platter 18 and having a lower shaft portion 62 extending from a motor 58 which is mounted to plate 64 and which may be actuated to rotate platter 18 to position any one of apertures 22 in vertical and horizontal alignment with weigh platform 16. Shaft 56 extends vertically through bore 56′ in the floor 32 of member 26 and has an upper end secured to the center of support plate 50.

Means 20 further includes lifting means 60 which includes horizontal support plate 64, rod block 66 fixedly secured to the underside of plate 64, and a pneumatic cylinder 68 having shaft 70 fixedly secured to block 66. Consequently, when pneumatic pressure is applied to cylinder 68, shaft 70 extends from the cylinder upwardly shifting rod block 66 and support plate 64 to which the platter-rotating means, including motor 58, is mounted. When the pneumatic pressure is released from cylinder 68, shaft 70, block 66, and support plate 64 move downwardly. Guide block 76 is fixedly secured to leg 77 of rod block 66 and includes an aperture 78 for receiving guide 74 extending upwardly from base 76 of analyzer 10. A second guide rod 72 extends slidably through an aperture in plate 64 such that the plate 64 and platter 18 rotatably coupled thereto are held in precise rotational alignment when the platter is raised and lowered by the actuation of cylinder 68.

By controlling pneumatic cylinder 68, support plate 64 may be vertically shifted between a raised load position shown in solid lines in FIG. 1, a somewhat lowered rotate position 64′, and a lowermost weigh position 64″. Because rotation device or motor 58 travels vertically with plate 64, it also moves vertically between a load position shown in FIG. 1, a rotate position 58′, and a weigh position 58″. Finally, because shaft 56 removes vertically with rotation device 58, platter 18 is vertically shiftable between a load position shown in FIG. 1, a rotate position 18′, and a weigh position 18″. In the load position, rack 18 is proximate the upper open end of furnace 12 to facilitate the positioning of crucibles 24 on apertures 22.

A latch 94 (FIG. 1) is pivotally mounted at 96 to a support bracket 98 and is pivotable between an unlocked position shown in FIG. 1 and a locked position 94′. Latch 94 includes a locking edge 100 which does not interfere with the movement of plate 64 when latch 94 is in its unlocked position. However, when rack 18 is in either rotate or weigh positions 18′ or 18″, respectively, latch 94 may be pivoted downwardly to its locked position wherein edge 100 is located directly above plate 64. Platter 18 may then not be raised to load position 18′ until latch 94 is unlocked.

Figure 4:
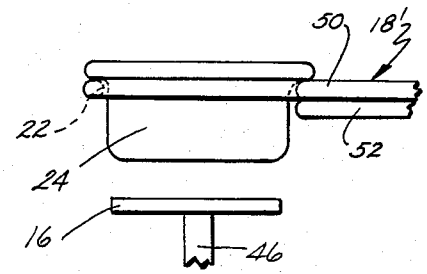
FIG. 4 is an enlarged view of the area within line IV in FIG. 1 with the sample platter in the rotate position.
Figure 5:
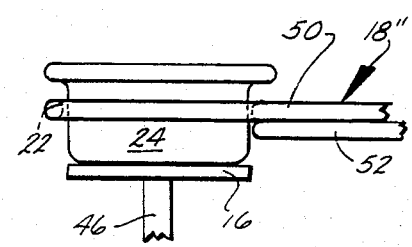
FIG. 5 is an enlarged view of the area within line IV in FIG. 1 with the sample platter in the weigh position.

FIGS. 4 and 5 demonstrate how crucible 24 is deposited on weigh platform 16. FIG. 4 shows sample platter 18 in the rotate position 18′ elevated above weigh platform 16, while FIG. 5 shows sample platter 18 in the lower weigh position 18″ wherein crucible 24 is deposited on weigh platform 16. As seen in FIG. 4, when rack 18 is in the rotate position, the rack is free to rotate within chamber 34 on shaft 56 above weigh platform 16. Motor 58 rotates rack 18 until one of the apertures 22 and crucible 24 thereon is generally vertically concentrically aligned with weigh platform 16. Device 58 then stops to maintain platter 18 in the desired angular orientation. Cylinder 68 is then deactuated to lower platform 64, device 58, and platter 18 into weigh positions 18″, 58″, and 64″ as shown in FIG. 5. As platter 18 moves downwardly to weigh position 18″, crucible 24 is deposited on the weigh platform. Rack 18 is maintained in this position for a sufficient period allowing balance 14 to determine a steady weight and provide an electronical output signal representative thereof. Cylinder 68 is then actuated to raise platter 18 to rotate position 18′ lifting crucible 24 off platform 16 as shown in FIG. 4, whereupon the platter is free to rotate again.

Crucible 24 is generally well known being a cup-shaped member preferably fabricated of porcelainized alumina. In the preferred embodiment, each crucible 24 weighs approximately 10 grams and is designed to contain a sample weighing approximately 1 gram. Consequently, the ratio of crucible weight to sample weight is approximately 10 to 1 although the sample weight may vary between 0.5 grams and 1.5 grams.

Figure 3:
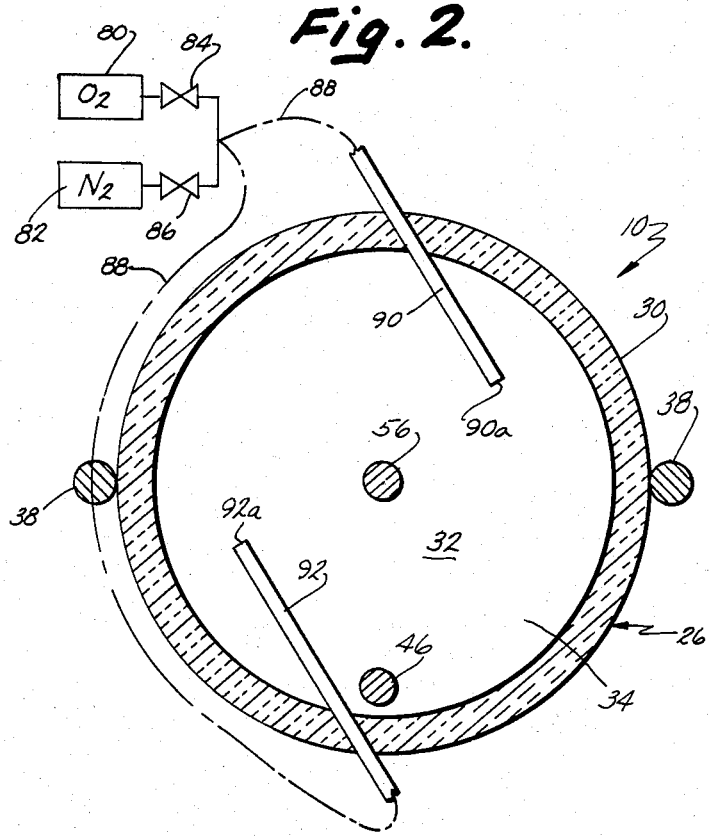
FIG. 3 is a view taken along plane III—III in FIG. 1.

FIG. 3 is a sectional view showing the gas introduction apparatus for selectively introducing elemental oxygen and elemental nitrogen into furnace chamber 34 to flood the chamber. Oxygen source 80 and nitrogen source 82 provide oxygen and nitrogen under a pressure of approximately 30 p.s.i. Sources 80 and 82 are controlled by valves 84 and 86, respectively, to introduce oxygen and nitrogen selectively into line 88 connected to nozzles 90 and 92, which extend through side wall 30 of lower member 26 and terminate in nozzle ends 90a and 92a, respectively. Nozzles 90 and 92 are arranged within chamber 34 to prevent the introduced gases from being directed against weigh platform 16 and shaft 46 which might affect balance accuracy.

Figure 6A:
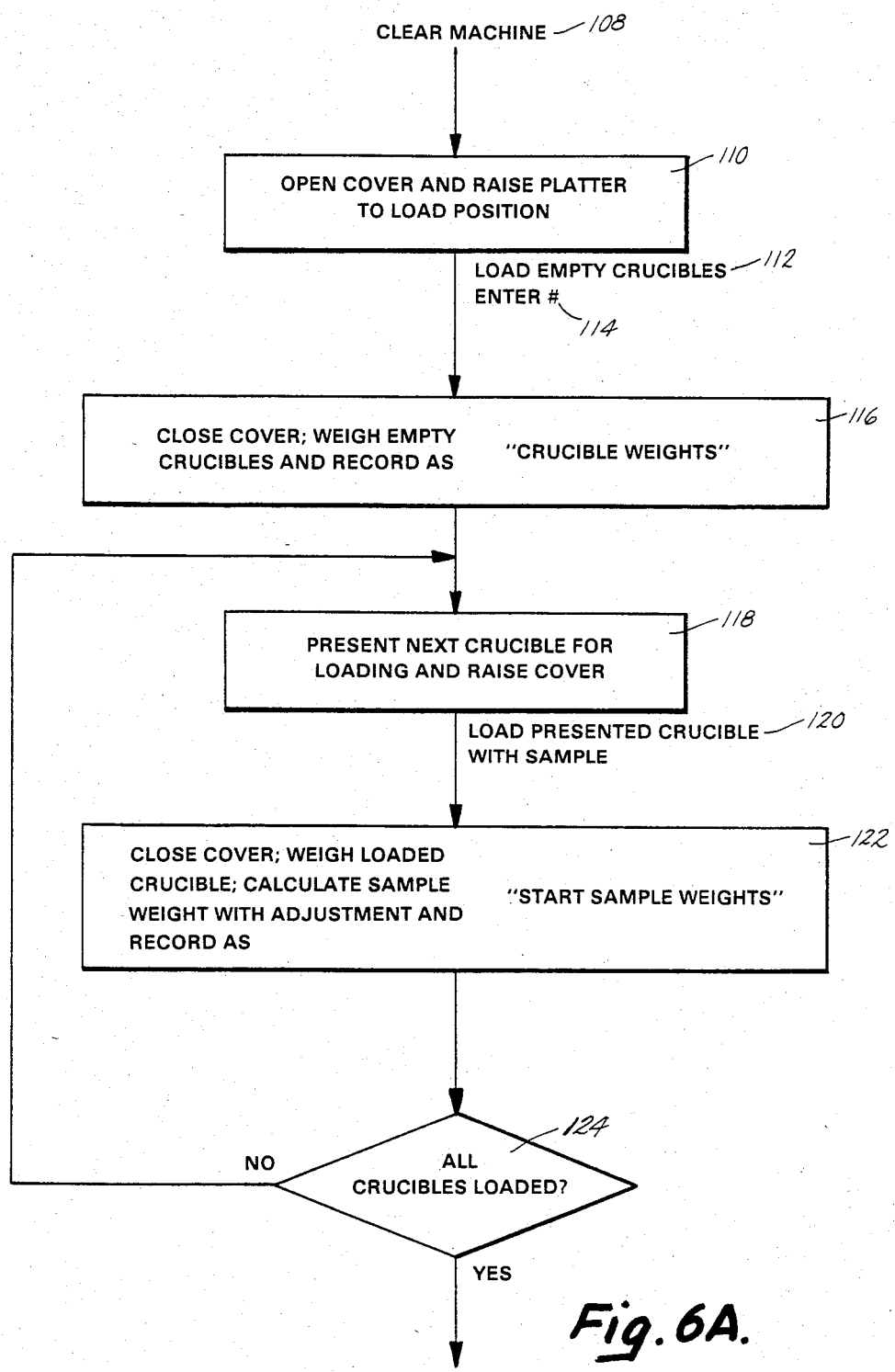
FIGS. 6A, 6B, and 6C are a flow diagram setting forth the control flow during an analyzer run.
Figure 6B:
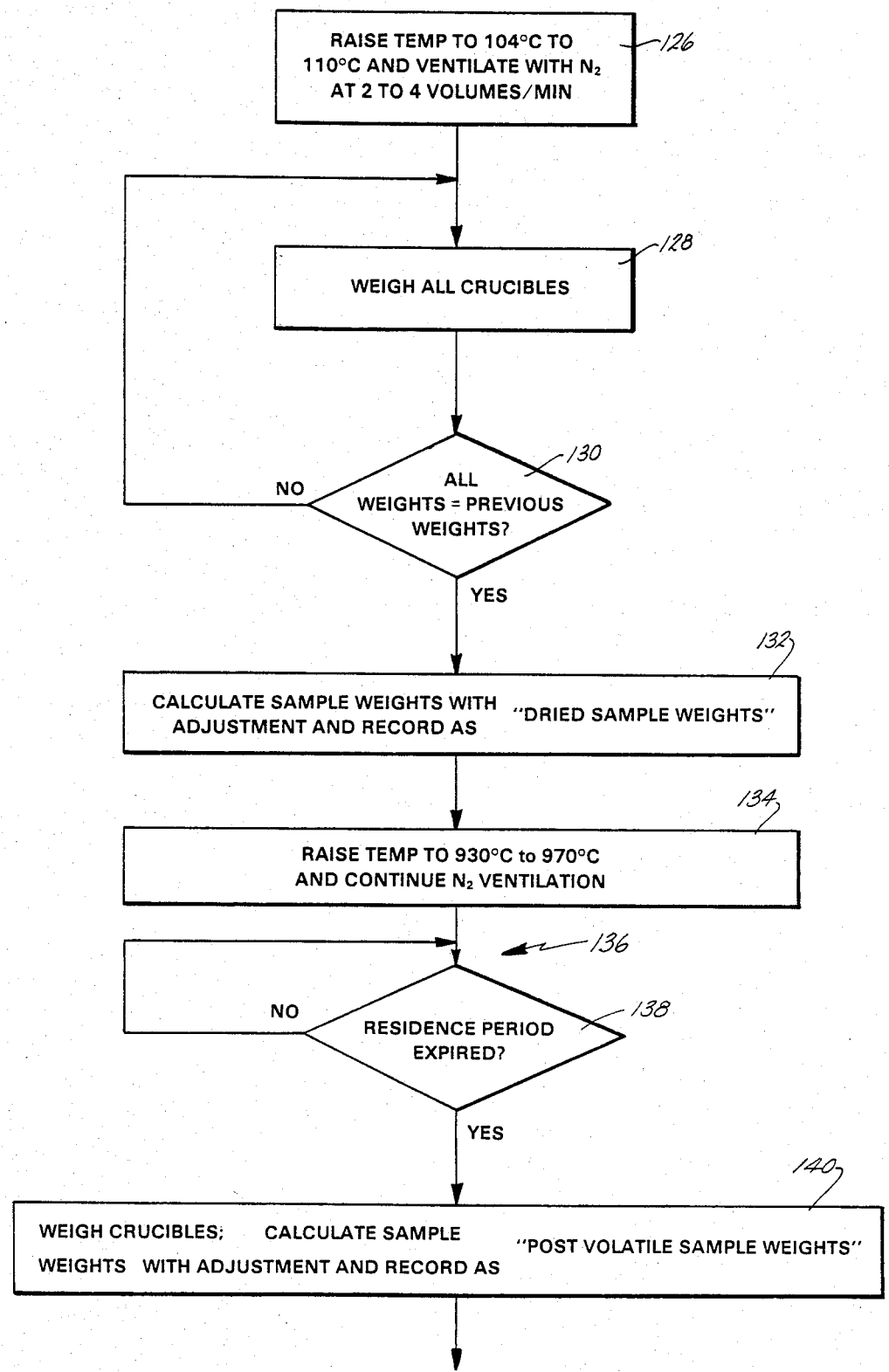

An electrical control circuit which, in the preferred embodiment of the invention comprises a computer 102 (FIG. 7) controls the analyzer 10. The computer is electrically coupled by conventional interface circuits to oxygen valve 84, nitrogen valve 86, cover pistons 38, latch 94, balance 14, shifting assembly 60, rotation device 58, and temperature control 108. Additionally, computer 102 is operatively connected to an input keyboard 104 and a printer 106. Computer 102 receives signals from keyboard 104, and balance 14 and generates signals to actuate the other devices connected thereto. The computer 102 is programmed to implement analyzer control as described herein, specifically with reference to FIGS. 6A-6C. In the preferred embodiment of the invention, the computer employed is an INTEL 8085 microprocessor. Temperature control 108 is a commercially available device including a thermocouple (not shown) located in chamber 34 to control the temperature therein.

Operation

FIG. 6 is a flow chart illustrating the program sequencing and control during an operational cycle of analyzer 10. All control is conducted by computer 102 which receives signals from keyboard 104 and balance 14 and issues control signals to oxygen valve 84, nitrogen valve 86, cover pistons 38, latch 94, shifting assembly 60, rotation device 58, and temperature control 108.

To initiate a machine cycle, the operator pushes an "analyze" key on keyboard 104. Computer 102 then supplies signals to cover pistons 38 to raise cover 28 to an open position 28" and to shifting assembly 60 to raise platter 18 to load position as indicated by step 110. The operator removes any crucibles 24 remaining on rack 18 from a previous analyzer cycle. The operator then positions an empty crucible 24 on plate 18 in zero-position aperture 22a as indicated by step 112. Additionally, an empty crucible 24 is positioned on platter 18 in a counter-clockwise direction from position zero 22a for each sample to be analyzed. For example, if three samples are to be analyzed, a total of four crucibles are placed on rack 18 and if seventeen samples are to be analyzed, eighteen crucibles are placed on rack 18. Each crucible 24 is positioned and aligned with one of the apertures 22, so that a total of twenty crucibles may be positioned in the twenty apertures. Crucible 24 in zero position 22a remains empty during the entire machine cycle, so that a maximum of nineteen samples may be analyzed during one analyzer cycle. After the empty crucibles are loaded, computer 102 supplies signals to cover pistons 38 to lower cover 28 to its closed position as indicated by step 116. Each of crucibles 24 on rack 18 is weighed 116 beginning with the crucible in zero position 22a. Computer 102 supplies control signals to shifting assembly 50 and rotation device 58 to sequentially, individually align each crucible 24 with weigh platform 16 and deposit the crucible on the weigh platform. The computer records the empty crucible weights as "crucible weights", and determines which of apertures 22 do not contain crucibles.

The individual crucibles are then individually presented 118 for sample loading by positioning the crucible over weigh platform 16. Cover 28 is then raised 118 to load position 28' and rack 18 is raised to the loading position whereupon the operator deposits 120 a sample such as coal or coke to be loaded within the pressed crucible. Shifting assembly 60 lowers plate 18 to weigh position 18", depositing the just-loaded crucible on weigh platform 16. Cover 28 is then immediately lowered 122 to its closed position. The weight at balance 14 is then noted and the "start sample weight" is calculated for that individual crucible by subtracting the "crucible weight" from the loaded crucible weight. Each crucible 24 is weighed immediately upon loading because moisture loss begins immediately. If the crucibles were not weighed until all were loaded, the starting weights would be somewhat inaccurate because moisture will have evaporated from the first crucibles loaded. After each sample-containing crucible has been weighed 122, computer 102 makes a decision indicated at decision box 124 based on whether all of the crucibles have been loaded. If the answer to this query is NO, the next crucible is presented for loading as indicated in box 118. If the answer is YES, flow control passes to box 126 in FIG. 6B.

After all of the crucibles have been loaded, the temperature within furnace 12 and more particularly within chamber 34, is elevated 126 to the regulated range 104° C. to 110° C., preferably 107° C. Additionally, nitrogen valve 86 is opened to flood, or ventilate, 126 chamber 34 with elemental nitrogen at approximately three furnace volumes, or nine liters, per minute. Consequently, a positive pressure is maintained within furnace chamber 34 during analysis. All of crucibles 24 are then individually weighed 128 in a predetermined sequence, namely beginning with the crucible in position zero 22a and continuing with the crucibles in a clockwise direction as viewed from above. Each time the control sequence passes test 128, all of crucibles 24 are weighed once. Each crucible weighing cycle time is approximately seven seconds, so that platter 18 makes one complete revolution at least every 140 seconds. After each weighing cycle, a decision is made as noted in block 130 based on the weights obtained from the two immediately preceding revolutions of platter 18. If all of the individual weights obtained from the most two recent weighings are equal, program control passes to test block 132. If the weighings are not yet equal, flow control returns to block 128 whereupon another weigh cycle is begun. As program control loops through blocks 128 and 130 until all sample weights are essentially constant, crucibles 24 are repeatedly, or continually, weighed by continually and individually depositing the crucibles on weigh platform 16.

Because the temperatures generated within furnace 12 affect the torque/weight linearity of balance 14, the crucible weights as indicated by the balance must be adjusted. Consequently, all readings from balance 14 during a weighing cycle are compensated by the percent change in the apparent weight of the dummy crucible in position zero 22a. Thus, if the "start weight" of the dummy crucible is 10.00 grams and a subsequent reading from balance 14 indicates a weight of 10.01 grams, all of the balance readings on that weighing cycle will be adjusted downwardly by one-tenth of one percent. Accordingly, readings from balance 14 are appropriately compensated for any torque-linearity variations from weighing cycle to weighing cycle.

The criteria for determining when the crucible weights are essentially constant is selected by the operator on keyboard 104 before crucible loading 112. For example, the operator may indicate that two weighing shall be considered essentially constant when within one-tenth of one milligram of one another. If the operator does not select a parameter, computer 102 will utilize a preprogrammed default value.

After all of the weights are essentially constant as determined in block 130, the sample weights are calculated, adjusted, and recorded 132 as "dried sample weights". The temperature within chamber 34 is elevated to 930° C. to 970° C., most preferably 950° C. and nitrogen ventilation is continued. The program control then passes to wait loop 136 to provide a residence period 138 during the volatile determination stage. The residence time is determined by two criteria. The first is to establish a residence period of a fixed time after a particular temperature has been reached within chamber 34. The second is to monitor the rate of change in weight of the samples at a particular temperature and terminate the residence period when this rate reaches a predetermined parameter value. In any event, when the selected residence period has expired, the program control passes to block 140, whereupon the crucibles are weighed, and the sample weights are calculated, adjusted, and recorded as "post-volatile sample weights". The residence periods will typically be from about five minutes to fifteen minutes with seven minutes currently employed.

Figure 6C:
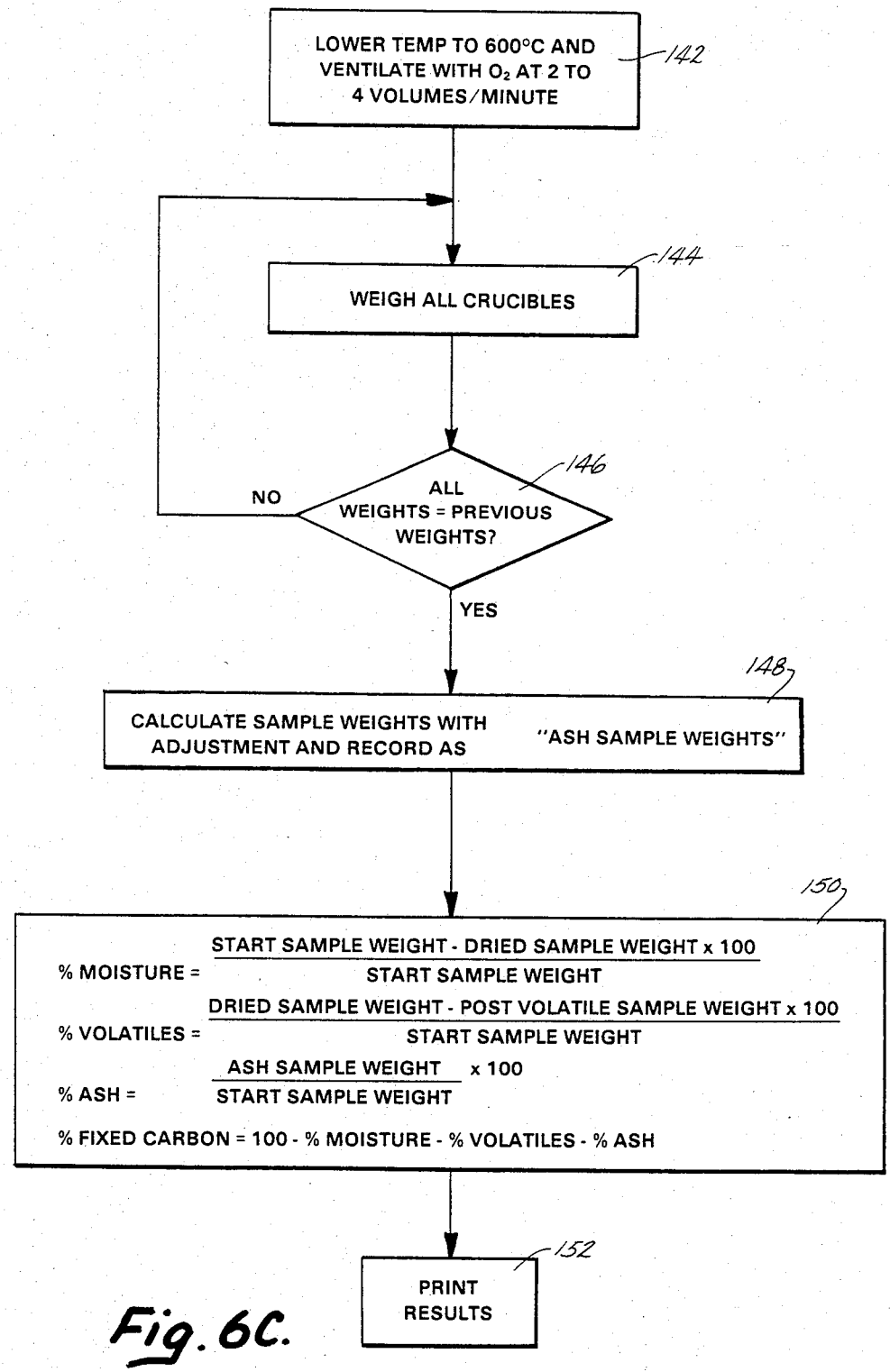
Figure 7:
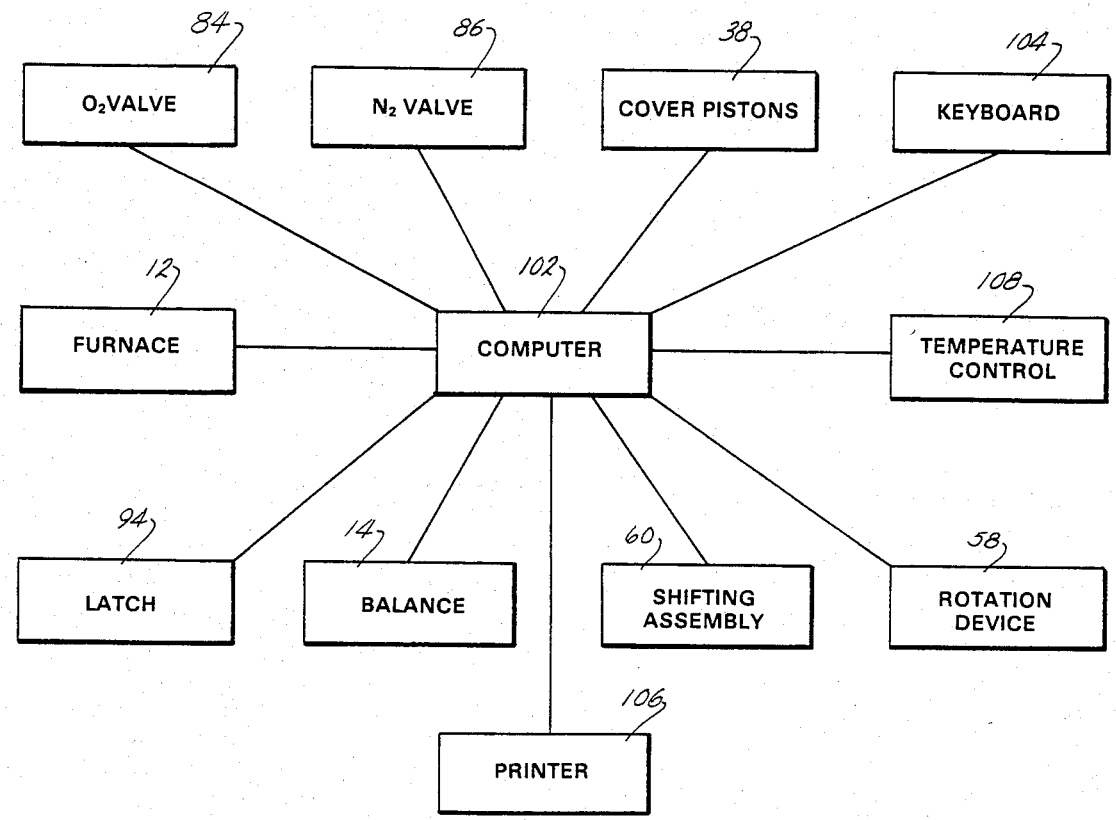
FIG. 7 is a schematic diagram showing the computer control for the analyzer.

Program control then enters an ash determination stage beginning with block 142 (FIG. 6C). The temperature within furnace 12 is then lowered to approximately 750° C. and nitrogen valve 86 is closed and oxygen valve 84 is opened to flood chamber 34 with oxygen at approximately three furnace volumes, or nine liters, per minute to facilitate oxidation of the samples. Crucibles 24 are weighed 144 as described above by cycling sample platter 18 through one complete revolution depositing each individual crucible on weigh platform 16. After each platter rotation, the weights obtained on that rotation are compared 146 with the weights obtained on the previous rotation to determine whether the sample weights are essentially constant. The same comparison criteria is applied as in box 130. If the weights are not yet constant, control returns to block 144 where the crucibles are again weighed. If the weights are essentially constant, control passes to block 148 where the sample weights are calculated, adjusted, and recorded by computer 102 as "ash sample weights".

The computer then performs well-known calculations 150 by conventional programming to determine the moisture, volatiles, ash, and fixed carbon content of each individual sample. The percent moisture is calculated for each sample to be the quantity "start sample weight" minus "dried sample weight" divided by "start sample weight", multiplied by 100. Percent volatiles are calculated for each sample by dividing the quantity "dried sample weight" minus "post-volatile sample weight" by "start simple weight", multiplied by 100. Percent ash is calculated for each samle by dividing "ash sample weight" by "start sample weight", multiplied by 100. Finally, percent fixed carbon is calculated by subtracting percent moisture, percent volatiles, and percent ash from 100. The percent moisture, percent volatiles, percent ash, and percent fixed carbon are then printed for each sample as indicated at 152, and the analyzer cycle is complete.

It should be understood that the above description is intended to be that of a preferred embodiment of the invention. Various changes and alterations might be made without departing from the spirit and broader aspects of the invention as set forth in the appended claims, which are to be interpreted in accordance with the principles of patent law, including the doctrine of equivalents.

The embodiments of the invention in which an exclusive property or privilege is claimed are defined as follows:

1. A fossil fuel proximate analyzer comprising:
   a furnace;
   a balance having a weigh platform positioned in said furnace;
   support means for supporting a plurality of crucibles in a generally horizontal, circular configuration, each of the crucibles holding a sample of a material to be analyzed;
   oxygen line means for selectively flooding said furnace with oxygen to facilitate oxidation of the samples during analysis, said oxygen line means including a first end to be coupled to an oxygen source, a second end communicating with said furnace, and a valve means between said first and second ends for controlling the flow of oxygen through said line means;
   rotation means for rotating said support means to sequentially vertically align the crucibles with said weigh platform;
   elevator means for vertically shifting said support means to deposit and remove the aligned crucible on and from said weigh platform;
   control means for controlling said rotation means and said elevator means to repeatedly weigh the crucibles sequentially;
   circuit means connected to said balance for monitoring the weights of the crucibles to monitor the weights of the samples, said circuit means including means for determining when the weights of the samples have reached a generally constant value indicating that a proximate analysis step is complete.

2. A proximate analyzer as defined in claim 1 wherein said support means comprises a generally planar plate.

3. A proximate analyzer as defined in claim 2 wherein said plate includes an aperture for receiving each of the crucibles.

4. A proximate analyzer as defined in claim 1 further comprising nitrogen line means for selectively flooding said furnace with nitrogen to prevent oxidation of the samples during analysis, said nitrogen line means including a first end to be coupled to a nitrogen source, a second end communicating with said furnace, and a valve means between said first and second ends for controlling the flow of nitrogen through said line means.

5. A proximate analyzer as defined in claim 1 wherein said furnace comprises a container with an upper open end and a cover, and further wherein said elevator means includes means for elevating said support means to a position proximate said upper open end to facilitate loading and unloading of the samples.

6. A proximate analysis device comprising:
   a furnace chamber;

a balance having a weigh platform positioned in said furnace chamber;

sample-holding means for supporting a plurality of crucibles, each of the crucibles containing a sample of a material to be analyzed;

oxygen line means for selectively flooding said furnace with oxygen to facilitate oxidation of the samples during analysis, said oxygen line means including a first end to be coupled to an oxygen source, a second end communicating with said furnace chamber, and a valve means between said first and second ends for controlling the flow of oxygen through said line means;

transport means for moving said sample-holding means to individually repetitively deposit the crucibles in a predetermined sequence on said weigh platform, said transport means including elevator means for vertically shifting said sample-holding means with respect to said weigh platform to deposit a crucible on, and lift a crucible off, said weigh platform;

control circuit means coupled to said balance for monitoring the individual weights of the crucibles to determine individual weight loss of the samples and calculate proximate analysis results, said control circuit means including computer means for determining when the weights of the samples have attained constant values indicating that a proximate analysis step is complete; and means coupled to said circuit means for displaying said results.

7. A device as defined in claim 6 further comprising gas line means for selectively flooding said furnace with a gas devoid of oxygen to prevent oxidation of the samples during analysis, said gas line means including a first end to be coupled to a gas source, a second end communicating with said furnace chamber, and a valve means between said first and second ends for controlling the flow of gas through said line means.

8. A device as defined in claim 6 wherein said furnace comprises a lower container having an upper open end and a cover for selectively closing said container, said cover movable between open and closed positions, and wherein said transport means includes means for elevating said sample-holding means to a position proximate said upper end when said cover is in said open position to facilitate loading of the crucibles.

* * * * *

UNITED STATES PATENT AND TRADEMARK OFFICE
CERTIFICATE OF CORRECTION

PATENT NO. : 4,522,788
DATED : June 11, 1985
INVENTOR(S) : George J. Sitek et al It is certified that error appears in the above-identified patent and that said Letters Patent is hereby corrected as shown below:

Column 3, line 17:
"at 28'" should be --as--

Column 3, line 36:
"circult" should be --circular--

Column 4, line 17:
"removes" should be --moves--

Column 6, line 9:
"pressed" should be --presented--

Column 7, line 63:
"simple" should be --sample--

Column 7, line 64:
"samle" should be --sample--

Signed and Sealed this

Fourteenth Day of January 1986

[SEAL]

Attest:

Attesting Officer

DONALD J. QUIGG

Commissioner of Patents and Trademarks